(12) United States Patent
Biedermann et al.

(10) Patent No.: US 7,131,995 B2
(45) Date of Patent: Nov. 7, 2006

(54) METHOD FOR THE MANUFACTURE OF A TUBULAR SPACER AND SPACER

(75) Inventors: Lutz Biedermann, VS-Villingen (DE); Jürgen Harms, Karlsruhe (DE); Helmar Rapp, Deisslingen (DE)

(73) Assignee: Biedermann Motech GmbH (DE)

( * ) Notice: Subject to any disclaimer, the term of this patent is extended or adjusted under 35 U.S.C. 154(b) by 0 days.

(21) Appl. No.: 10/647,096

(22) Filed: Aug. 21, 2003

(65) Prior Publication Data

US 2004/0098128 A1    May 20, 2004

(30) Foreign Application Priority Data

Aug. 21, 2002    (DE)    ................. 102 38 306

(51) Int. Cl.
*A61F 2/30*    (2006.01)
(52) U.S. Cl. ................................... 623/23.46
(58) Field of Classification Search ............ 623/23.45, 623/23.46, 23.47, 16.11, 17.11
See application file for complete search history.

(56) References Cited

U.S. PATENT DOCUMENTS

| | | | |
|---|---|---|---|
| 3,710,789 A | | 1/1973 | Ersek |
| 4,820,305 A | | 4/1989 | Harms et al. |
| 5,211,664 A | | 5/1993 | Tepic et al. |
| 5,380,328 A | | 1/1995 | Morgan |
| 5,609,637 A | * | 3/1997 | Biedermann et al. .... 623/17.16 |
| 5,897,593 A | * | 4/1999 | Kohrs et al. ............ 623/17.16 |
| 5,972,031 A | * | 10/1999 | Biedermann et al. .... 623/17.16 |
| 6,585,770 B1 | * | 7/2003 | White et al. ............ 623/17.11 |
| 6,660,038 B1 | * | 12/2003 | Boyer et al. ............ 623/17.15 |
| 2001/0035038 A1 | | 11/2001 | Ose |

FOREIGN PATENT DOCUMENTS

| | | |
|---|---|---|
| DE | 28 42 847 A1 | 4/1980 |
| DE | 295 01 042.8 | 5/1995 |
| DE | 195 04 867 | 2/1996 |
| DE | 195 04 867 C1 | 2/1996 |
| EP | 0 268 115 | 5/1988 |
| EP | 0 720 840 B1 | 3/1998 |
| EP | 0 853 931 | 7/1998 |
| FR | 1.527.214 | 5/1968 |
| WO | WO 99/32055 | 7/1999 |
| WO | WO 99/51171 | 10/1999 |
| WO | WO 00/24341 | 5/2000 |
| WO | WO 02/34168 | 5/2002 |
| WO | WO 02/085552 | 10/2002 |
| WO | WO 03/039784 | 5/2003 |

\* cited by examiner

*Primary Examiner*—Alvin J. Stewart
(74) *Attorney, Agent, or Firm*—Christie, Parker & Hale, LLP

(57) ABSTRACT

A tubular spacer and a method for the manufacture of the spacer is described. The tubular spacer has a first rim on a first end, a second rim on its opposite second end, and a jacket extending between said first and said second rims. The jacket has a tapered section adjacent to at least one end. The spacer is suitable for use in tubular bone surgery where it is necessary that the spacer adapts to different bone cross-sections. To make this tubular spacer, a cylinder having a tubular jacket body is expanded and/or narrowed at one or both of its ends. Methods for using the spacer as well as kits for making the spacers are described.

20 Claims, 3 Drawing Sheets

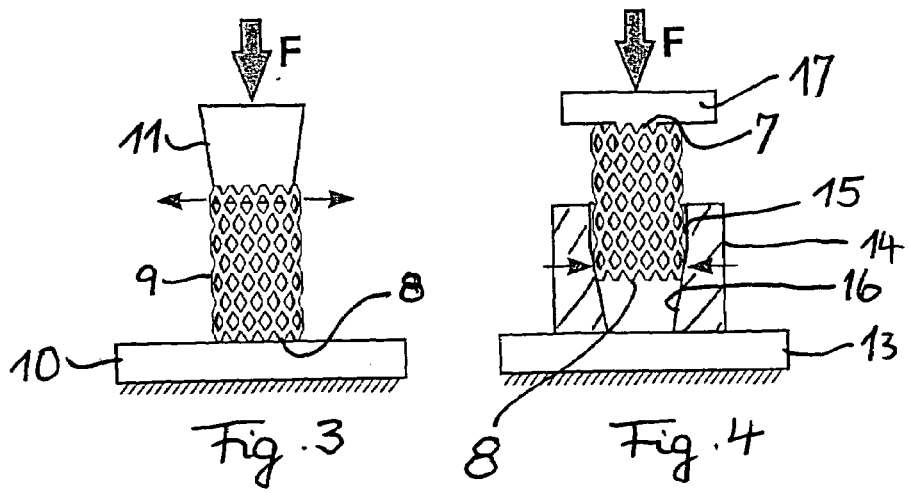
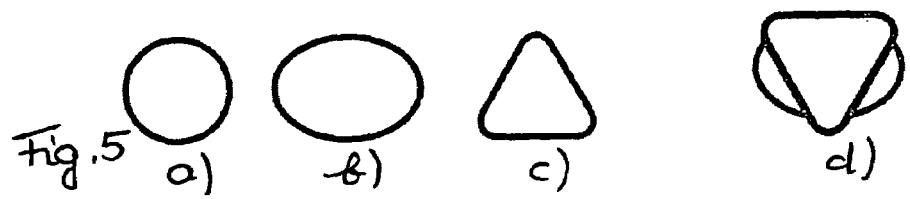
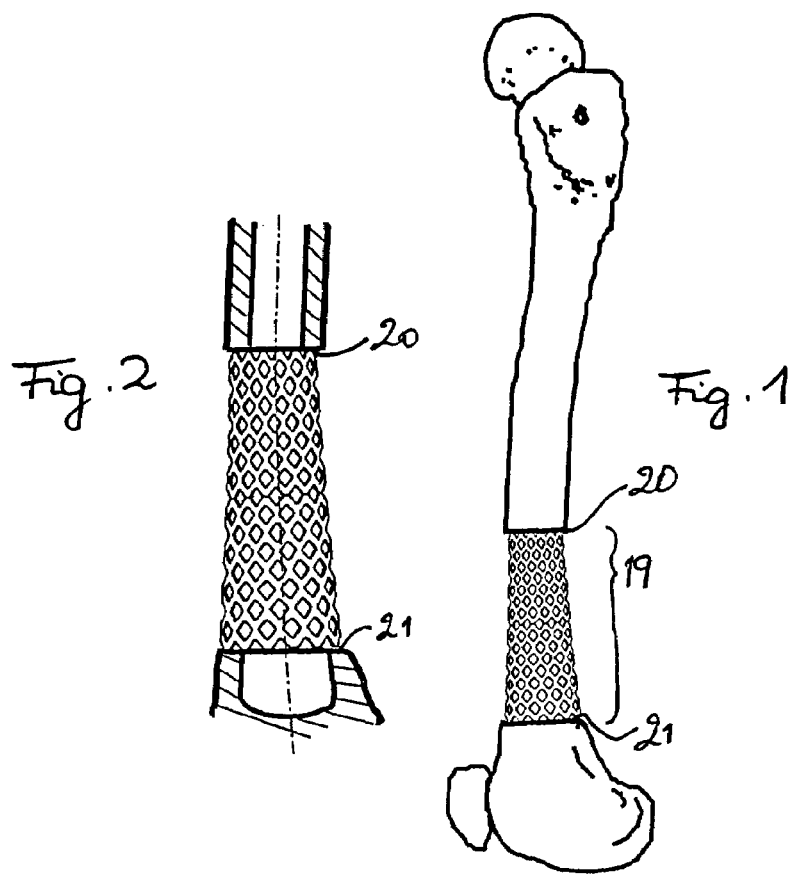

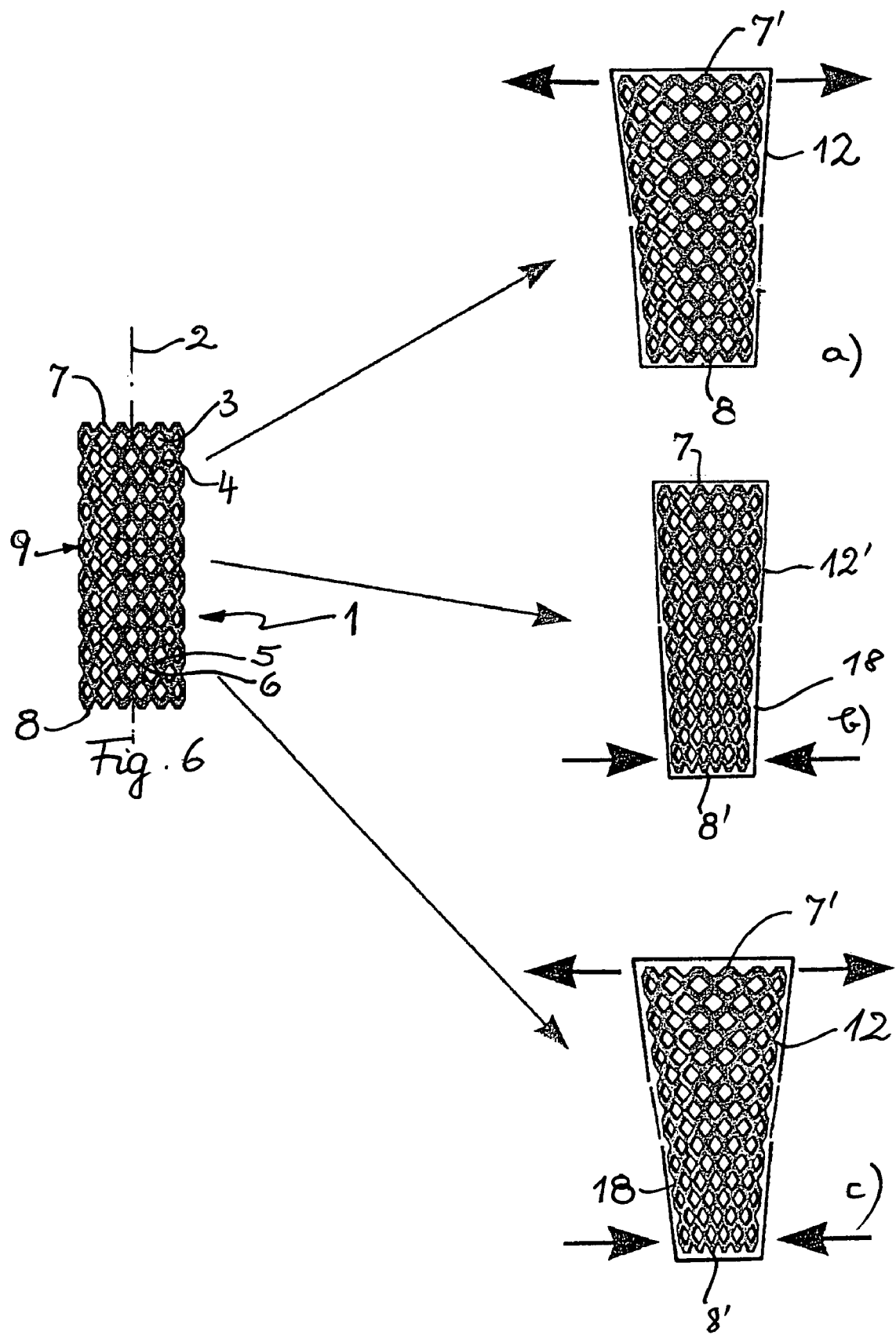

US 7,131,995 B2

METHOD FOR THE MANUFACTURE OF A TUBULAR SPACER AND SPACER

FIELD OF THE INVENTION

The invention relates to a tubular spacer for bone defects having a first rim at its first end and a second rim at its opposite second end and method for the manufacture thereof wherein at least one of the ends is modified to have a tapered section. More particularly, the invention relates to such a spacer having a tubular jacket provided with recesses.

BACKGROUND OF THE INVENTION

A spacer is described in DE 195 04 867 C or U.S. Pat. No. 5,702,451. This spacer is used mainly to replace a vertebra or intervertebral disk. The spacer is made from a cylindrical tube which has the same diameter at its opposite ends. EP 0 720 840 A describes a connector for vertebrae differing in size and cross-section by providing a spacer comprising at least two jacket-shaped elements with different cross-sections and one connecting element to connect the jacket-shaped elements. The individual elements are all provided with cylindrical shape. These spacers are suited for use in spinal surgery, however, their usefulness with tubular bones is limited.

It is, therefore, desirable to provide a tubular bone spacer and a method for the manufacture thereof that is especially well-suited for use in tubular bone surgery.

SUMMARY OF THE INVENTION

The present invention provides a spacer for bone defects comprising a tubular jacket, preferably with recesses, and having a first rim on its first end face and a second rim on its opposite second end face wherein one of the ends of the tubular jacket is modified to form a tapered section. The invention also provides a method for the manufacture of the tubular spacer for bone defects wherein the spacer is formed by making or providing a cylinder of jacket material, cutting the jacket material to a desired length and modifying the opening of a rim at one end of the cylinder.

In one embodiment, the spacer is formed by expansion of a cylinder with the expansion commencing at one end. In another embodiment of the invention, the spacer is formed by narrowing of a cylinder with the narrowing commencing at one end. In yet another embodiment, the spacer is made by an expansion proceeding from one end of the cylinder and a narrowing proceeding from the other end.

Thus, the cross-section of the expanded and/or narrowed portions of the spacer differs from the cross-section of the original cylinder of jacket material. In some preferred embodiments, a certain portion of the spacer has a cross section that remains unchanged from the original cylinder of jacket material.

A preferred method for expanding the cross section of the spacer is by pushing a mandrel into the end of a cylinder. A preferred method for narrowing the cross section of the spacer is by pushing the end of a cylinder into a hollow die or mold. Another preferred method for making spacers in accord with the present invention is to expand one end of the spacer by pushing a mandrel into it while narrowing the opposite end simultaneously by pushing the opposite end into a hollow mold.

Preferably, the spacer for bone defects comprises a tubular jacket with a number of openings or recesses distributed in the jacket wall. In one embodiment, one of the ends of the tubular jacket is expanded or narrowed. In another embodiment, one of the ends of the tubular jacket is expanded and the other end is narrowed. In yet other embodiments, both ends are expanded or narrowed. In a preferred embodiment, the recesses comprise a multitude of rhomboid-shaped recesses arranged adjacent to each other in the direction of the circumference of the tubular body. Thus, the jacket surface preferably comprises a lattice of rhomboid openings or recesses.

Preferably, the spacers are made so that opposite ends possess diameters or cross sectional areas of a size that suits or corresponds to the bone parts to be connected.

The invention also provides a method for repairing bones or connecting bone parts using the spacers of the present invention. The method comprises providing a tubular spacer in accord with the present invention having a length suitable for connecting two bone parts, inserting the spacer between the two bone parts to be connected, providing a compression force on the spacer between the bone parts and allowing tissues to grow over the spacer and connect the bone parts.

The invention further provides kits for bone repair. The kits provide one or more lengths of cylindrical tubular jacket material, one or more abutment plates, one or more mandrels, and one or more hollow dies for expanding or narrowing the ends of a cut length of tubular spacer on site as desired. Preferably, lengths of cylindrical jacket material are supplied having different diameters. Also, it is preferred that the cylindrical tubular jacket material have recesses in the jacket wall to promote tissue growth when the spacer is used.

Further features and characteristics of the invention are evident from the description of embodiments and accompanying figures.

BRIEF DESCRIPTION OF THE DRAWINGS

FIG. 1 illustrates a side view of a tubular bone with the spacer inserted;

FIG. 2 illustrates a magnified view of a portion of FIG. 1, in which a section through the bone is depicted;

FIG. 3 illustrates a schematic diagram of a device for expansion of one end of a spacer;

FIG. 4 illustrates a schematic diagram of another device for narrowing one end of a spacer;

FIGS. 5a)–5d) illustrate various cross sectional shapes for the ends or rims of the spacers made in accord with the present invention;

FIG. 6 illustrates a cylindrical spacer that can be modified to make spacers in accord with the present invention;

FIGS. 6a)–6c) illustrate three different spacers according to the invention made from the spacer of FIG. 6;

DETAILED DESCRIPTION OF THE INVENTION INCLUDING PREFERRED EMBODIMENTS

Figure 7:
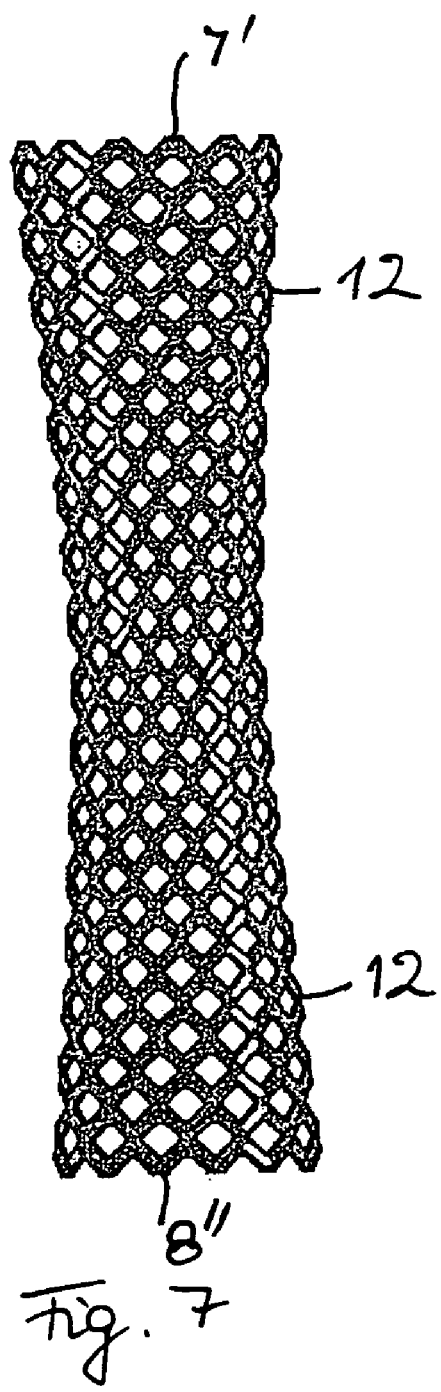
FIG. 7 illustrates a modified form of a spacer in accord with the invention having both ends expanded.

As is depicted most clearly in FIG. 6, a preferred method for making tubular spacers in accord with the present invention uses as the starting material a cylindrical tube of jacket material as a spacer body, the length of which corresponds to the distance between the bone parts to be connected or to the length or distance that needs to be bridged.

The cylinder can be provided as a tubular body with no recesses. However, it is preferred that the cylinder be provided with recesses in order to facilitate the in-growth of bone tissue or bone material. The figures depict a particularly preferred embodiment of the starting material with rhomboid-shaped recesses 3, 4.

Initially, preferably jacket 1 is provided in the shape of a right circular cylinder 9. The jacket wall preferably is unthreaded and provided with rhomboid-shaped recesses 3, 4 having a longitudinal diagonal that extends parallel to jacket axis 2. Thus, the horizontal diagonal of the rhomboid extends in a plane perpendicular to the axis 2. Adjacent rows of these rhomboid-shaped recesses are staggered along jacket axis 2 by one-half the height (i.e., longitudinal length) of the rhomboid. This arrangement provides for the generation of a network of banded strips 5, 6 which intersect at an acute angle, the banded strips 5, 6 being inclined with respect to the longitudinal diagonal of rhomboids 3, 4 with identical angles of inclination. Upper rim 7 and lower rim 8 both extend in a plane orthogonal to longitudinal axis 2.

In a first embodiment of a spacer to be manufactured, the lower rim is to maintain both the shape and the size of the original lower rim of the starting cylinder, whereas the diameter of upper rim 7' is to be larger by a predetermined degree.

For this purpose, right circular cylinder 9 (as shown in FIG. 6) is the starting material. As is depicted best in FIG. 3, cylinder 9 is placed with its lower rim on an abutment 10. A mandrel 11 is inserted in the open end (or face) bordered by upper rim 7 and driven-in by the action of a force, F, depicted schematically, acting along the direction of jacket axis 2 in the direction of abutment 10 until the desired expansion shown in FIG. 6a) is attained. As shown in FIG. 6a), the use of the mandrel for expansion provides for the expansion proceeding such that section 12, into which the mandrel is driven, conforms to the shape of the mandrel. As shown in FIG. 3, the mandrel is shaped like a truncated cone so that section 12 assumes a corresponding shape and diameter of the upper rim becomes larger than that of lower rim 8 by the corresponding degree.

In another embodiment, shown in FIG. 6b), it is desired for section 12' bordering upper rim 7 to remain unchanged, which means that especially the diameter of the upper rim remains unchanged. In contrast, lower rim 8 of starting cylinder 9 is to be changed. For this purpose, an abutment 13 with a hollow die 14 (or mold) is used. At its free end, which is opposite from the actual abutment 13, the hollow die 14 has a section 15, the diameter and shape of which correspond to the outer dimensions of starting cylinder 9. Adjacent to this section 15 is a second section 16, which tapers off towards the base (i.e., the abutment 13) in a truncated cone-like fashion. Starting cylinder 9 is inserted into die 14 with its lower rim 8 directed toward the actual abutment 13, as shown in FIG. 4. Upper abutment 17 engaging on the opposite upper rim 7 allows a force F, depicted schematically, to be applied in the direction towards abutment 13, i.e., in the direction of the lower rim 8. Thus, the force F causes the section of the cylinder adjacent to rim 8 to be narrowed until a desired predetermined dimension is attained. Thus, a narrowed section 18' with narrowed rim 8', as depicted in FIG. 6b), is generated. In the embodiment shown in FIG. 4, abutment 17 is provided with a guiding cylinder (not shown) pointing into the cylinder for stable positioning and application of the force.

In a further embodiment, shown in FIG. 6c), upper rim 7 of starting cylinder 9 is expanded in a first step to generate a section 12, for example, as was done to form the embodiment according to FIG. 6a), if desired. This expansion is brought about by use of the method described with reference to FIG. 3. Subsequently, lower rim 8 is narrowed using the device and method described with reference to FIG. 4, such that the lower rim and the area adjacent to it assume a narrowed shape like section 18' in FIG. 6b). Alternatively, both the expansion of one end and the narrowing of the opposite end may be accomplished simultaneously by inserting one end into the hollow die and inserting the mandrel into the opposite end before applying the force. More precise control of the expansion and narrowing can be achieved by separate performance of the steps.

This procedure allows spacers differing in shape to be formed from a starting cylinder, 9, such that the spacers can be adapted to the respective section-to-be-bridged 19 (FIG. 1) between two bone ends 20, 21 differing in shape and size.

Starting cylinder 9 can be provided with any of a number of pre-made cross-sectional shapes, although a circular cross-section is presently preferred. Mandrel 11 and hollow die 14 also can possess any of a number of cross-sectional shapes and angles of taper such that sections 12 and 18, generated by their action, possess a similar shape, for example, the circular shape depicted in FIG. 5a) or an oval or triangular shape as depicted in FIGS. 5b), 5c). The particular cross sectional shape is limited only by the imagination of the designer and practical limitations of the spacer shaping process being used.

Alternatively, if it is desired to provide different shapes to upper rim 7 and lower rim 8, then one can select mandrel 11 with one cross sectional shape and hollow die 14 with a different cross sectional shape such that, for example, one rim assumes an oval shape and the other rim assumes a triangular shape, as depicted in the example shown in FIG. 5d).

As mentioned above, starting cylinder 9 can be provided with recesses 3, 4 of various designs. The design of rhomboid orifices provides the particular advantage that the shape-changed rims, 7', 8', generated by expansion or narrowing also possess a notched rim that can support the formation of a particularly stable connection between adjacent bone ends 20, 21 and rims 7', 8'.

FIG. 7 shows an embodiment of a tubular spacer of the present invention, in which both the upper and the lower rim were expanded by use of the procedure illustrated with reference to FIG. 3 on both ends of the starting cylinder to the effect that the spacer possesses sections 12 on both of its ends that are expanded to assume a cone-shape, i.e., both ends expand toward the respective rims 7', 8".

Figure 8:
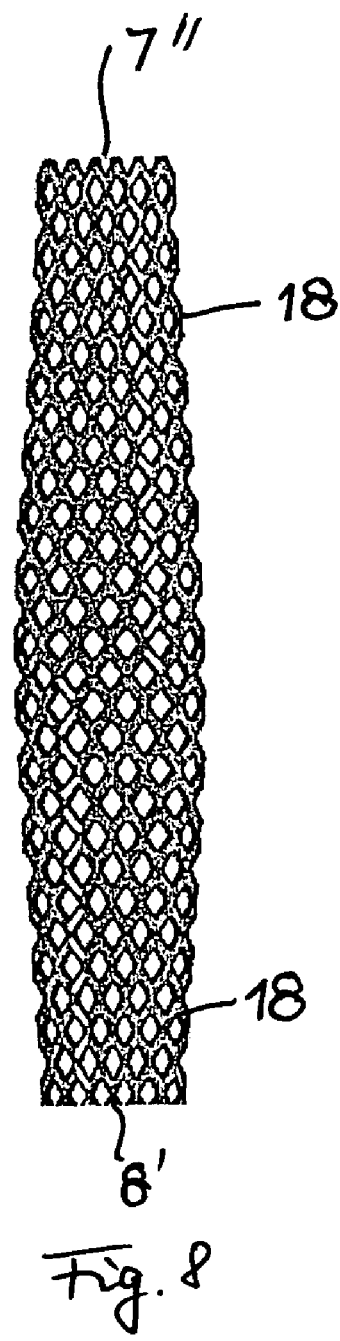
FIG. 8 illustrates another modified form of a spacer in accord with the invention having both ends having both ends narrowed.

FIG. 8 shows an embodiment of a tubular spacer of the present invention, in which the opposite ends were narrowed using the method illustrated with reference to FIG. 4 on both ends of the starting cylinder to the effect that the spacer dimensions in the middle of the spacer correspond to those of starting cylinder 9, whereas the sections adjacent to the middle possess sections 18 that narrow towards the respective rims ", 8'.

The devices shown in FIGS. 3 and 4 are depicted in schematic illustrations only. In a preferred embodiment, for example, abutment 10 and mandrel 11 on one side, or upper abutment 17 and abutment 13 with hollow die 14 on the other side may each be connected by means of levers (not shown) in the manner of a knuckle-joint press.

Body-compatible materials well known to those skilled in the art are selected as the materials for the spacers, in particular, steel or titanium and their respective alloys. Depending on the degree of expansion or narrowing, any tension or other stresses generated in the material can be removed by a heat treatment, if desired. Starting cylindrical spacer material, which can be cut and modified, can be any conventional cylindrical bone spacer material. Suitable such material is described, for example, in U.S. Pat. No. 5,702,451, the disclosure of which is hereby incorporated by reference.

The use of the spacers described above involves the application of basically known additional supporting measures for transfer of the load. For instance, in order to generate a pulling force, a plate is screwed to the two bone ends to be connected and a tension force applied using the plates or the bone parts are connected in a known manner by means of a marrow nail in order to generate a compressive force on the spacer.

In accord with the present invention, bone repair is accomplished by providing a length of spacer suitable for connecting two separated bone parts, inserting the spacer between the two bone parts to be connected, providing a compression force on the spacer between the bone parts and allowing tissues to grow over the spacer and connect the bone parts. Preferably, cylindrical spacer material is provided, which can be cut to the desired length for the bone repair or bone connection. After the cylindrical spacer material is cut to the desired length, the ends of the cut length are expanded or narrowed as desired, for example by methods described hereinabove.

The modified spacer then can be filled with bone chips or artificial bone material for example tricalciumphosphate or bone cement or a mixture thereof and is inserted between the bone parts to be repaired or connected and a compressive force applied to the spacer by additional means such as described above. Any conventionally known structures such as bone plates, bone screws, connecting rods, etc. can be used to apply the compressive force, as is well known to those skilled in the art. Then, tissues are allowed to grow over the spacer and connect the bone parts using conventional procedures well known to those skilled in the art. Preferably, the spacer material used has recesses.

Conveniently, kits can be provided containing lengths of cylindrical jacket material having different diameters. The kits also contain abutment plates, one or more mandrels, and one or more hollow dies such as described above with reference to FIGS. 3 and 4. Thus, the cylindrical spacer material can be cut to the desired length in an operating room and the ends expanded or narrowed as desired on site for a particular bone repair.

The invention has been described in detail including the preferred embodiments thereof. However, those skilled in the art, upon consideration of the present disclosure including the drawings and the descriptions herein, may make modifications and improvements within the spirit and scope of the present invention.

What is claimed is:

1. A spacer for bone defects comprising a tubular body having a first end, a first rim at the first end, a second end, a second rim at the second end, a longitudinal axis, an unthreaded jacket wall extending in the direction of said longitudinal axis from said first rim to said second rim, said jacket wall having a first body section adjacent the first rim and a second body section adjacent the second rim, wherein said first body section has a tapered shape, wherein the jacket wall comprises a plurality of recesses.

2. The spacer of claim 1, wherein the recesses are rhomboid shaped recesses.

3. The spacer of claim 2, wherein the rhomboid-shaped recesses are arranged in groups such that the recesses in a group are adjacent to each other in the direction of the circumference.

4. The spacer according to claim 3, wherein the jacket wall comprises the shape of a rhomboid lattice.

5. The spacer of claim 1, wherein the tapered shape diverges from the longitudinal axis in a direction of the first end.

6. The spacer of claim 1, wherein the tapered shape converges toward the longitudinal axis in a direction of the first end.

7. The spacer according to claim 1, wherein said second body section has a tapered shape and wherein the tapered shape of the first body section diverges from the longitudinal axis in a direction of the first end and wherein the tapered shape of the second body section converges toward the longitudinal axis in a direction of the first end.

8. A method for connecting two bone parts, the method comprising:
providing a length of tubular spacer sufficient to connect the bone parts, the spacer comprising a tubular body having a first end, a first rim at the first end, a second end, a second rim at the second end, a longitudinal axis, a jacket wall extending in the direction of said longitudinal axis from said first rim to said second rim, said jacket wall having a first body section adjacent the first rim and a second body section adjacent the second rim, wherein said first body section is tapered;
inserting the length of tubular spacer between the bone parts to be connected; and
applying a compression force to the tubular spacer positioned between the two bone parts
wherein the step of providing a length of tubular spacer comprises:
providing cylindrical tubular jacket material;
cutting the cylindrical tubular jacket material to said length; and
expanding or narrowing at least one of the first and second ends of the tubular spacer to adjust to the bone parts being connected.

9. The method according to claim 8, comprising a step of filling the spacer with bone chips or artificial material.

10. The method according to claim 8, wherein the expanding or narrowing step comprises expanding a rim of the tubular body.

11. The method according to claim 8, wherein the expanding or narrowing step comprises expanding a section of the body adjacent to the first rim with the expansion commencing at the first end.

12. The method according to claim 8, wherein the expanding or narrowing step comprises narrowing a rim of the tubular body.

13. The method according to claim 8, wherein the expanding or narrowing step comprises narrowing a section of the body adjacent to the first rim with the expansion commencing at the first end.

14. The method according to claim 8, wherein the expanding or narrowing step comprises expanding the first rim of the tubular body and narrowing the second rim of the tubular body.

15. The method according to claim 8, wherein the expanding or narrowing step comprises expanding a first section of the body adjacent to the first rim with the expansion commencing at the first end and narrowing a second section of the body adjacent to the second rim with the expansion commencing at the second end.

16. The method according to claim 8, wherein the expanding or narrowing step comprises expanding a first section of the body adjacent to the first rim with the expansion commencing at the first end and expanding a second section of the body adjacent to the second rim with the expansion commencing at the second end.

17. The method according to claim 8, wherein the expanding or narrowing step comprises narrowing a first section of the body adjacent to the first rim with the expansion commencing at the first end and narrowing a second section of the body adjacent to the second rim with the expansion commencing at the second end.

18. The method according to claim 8, further comprising shaping a cross-section of the first rim to differ from a cross-section of the second rim.

19. The method according to claim 8, wherein the expanding or narrowing step comprises expanding a first section of the body by pushing-in a mandrel.

20. The method according to claim 8, wherein the expanding or narrowing step comprises expanding a first section of the body by pushing the first end into a hollow die.

* * * * *